United States Patent [19]

Tovrog et al.

[11] 4,191,696
[45] Mar. 4, 1980

[54] OXIDATION PROCESS USING METAL NITRO COMPLEX

[75] Inventors: Benjamin S. Tovrog, Parsippany; Steven E. Diamond, Randolph; Frank Mares, Whippany, all of N.J.

[73] Assignee: Allied Chemical Corporation, Morris Township, Morris County, N.J.

[21] Appl. No.: 927,194

[22] Filed: Jul. 24, 1978

[51] Int. Cl.$^2$ .................. C07C 5/48; C07C 27/12; C07C 29/02; C07C 45/16
[52] U.S. Cl. ............... 260/348.33; 260/586 P; 260/590 R; 260/591; 260/592; 260/596; 260/606.5 P; 260/687 R; 260/687 H; 568/700; 568/811; 568/821; 568/833; 568/838; 568/839; 568/860; 585/430
[58] Field of Search ............ 260/586 P, 590 R, 591, 260/592, 596, 606.5 P, 348.33, 668 R, 668 D, 687 R, 687 H; 568/700, 811, 821, 833, 838, 839, 860

[56] References Cited

U.S. PATENT DOCUMENTS

| | | | |
|---|---|---|---|
| 3,404,185 | 10/1968 | Thomas et al. | 260/586 P |
| 3,458,547 | 7/1969 | Coffey et al. | 260/586 P |
| 3,927,111 | 12/1975 | Robinson | 260/590 R |
| 3,965,185 | 6/1976 | Young | 260/592 |
| 3,981,921 | 9/1976 | Bohmsholdt et al. | 260/596 |
| 3,989,801 | 11/1976 | Field et al. | 423/385 |
| 4,026,947 | 5/1977 | Costantini et al. | 260/586 P |
| 4,046,813 | 9/1977 | Brenner | 260/586 P |
| 4,100,208 | 7/1978 | Maspero et al. | 260/596 |
| 4,104,312 | 8/1978 | Angstadt et al. | 260/586 P |

OTHER PUBLICATIONS

Keene et al, "J.A.C.S.", vol. 99, p. 14 (1977).
Clarkson et al, "Inorg. Chem.," vol. 12, pp. 1528–1534 (1973).

*Primary Examiner*—Norman Morgenstern
*Attorney, Agent, or Firm*—Robert A. Harman

[57] ABSTRACT

A new liquid phase oxidation process in which a metal nitro complex transfers an oxygen atom from the nitro ligand to a substrate; especially such process conducted cyclically or catalytically using molecular oxygen as the oxygen source. Metal nitrosyl complex is formed as a coproduct together with an oxidation product of the substrate. In a catalytic process, molecular oxygen maintains a concentration of nitro ligand in the reaction mixture. In a cyclic process, nitrosyl ligand of the metal nitrosyl coproduct is reoxidized by molecular oxygen in presence of a monodentate base such as pyridine to nitro ligand; and the nitro complex, thus regenerated, can be used again to oxidize the substrate, In particular the metal is a Group VIII metal, especially cobalt and the nitro complex is pyridine cobalt nitro saloph. To accelerate oxidation of the substrate at given temperature, a cocatalyst is included in the reaction mixture, e.g. an organic complex of a transition metal such as Mo(VI), Pd(II), or a compound of a trivalent metallic element with an element of Group VII, such as the compound $BF_3$.

11 Claims, No Drawings

OXIDATION PROCESS USING METAL NITRO COMPLEX

BACKGROUND OF THE INVENTION

This invention relates to a new oxidation process, using metal nitro complexes (also called metal nitrito complexes) to transfer oxygen to a substrate. Especially the invention relates to oxidation using cobalt nitro complexes and molecular oxygen as the oxygen source.

Cobalt nitro complexes obtained by air oxidation of the nitrosyl complexes in presence of a nitrogen or phosphorus base are known (Inorganic Chemistry, volume 12 of 1973, pages 1528–1534); but no process has heretofore been proposed, so far as we are aware, wherein such complexes function to bring about the oxidation of a substrate.

In the prior art certain oxidation processes using molecular oxygen as the oxygen source are known. In general such processes operate by adsorption on metal oxide catalyst from vapor phase; or proceed in vapor phase or liquid phase by a pathway involving peroxide and free radicals. Such reactions may not be selective for oxidation of particular structures to particular products and/or may not be broadly applicable to a given chemical class of compounds.

Prior to the filing of this application, chemically catalyzed electrochemical oxidation has been disclosed in presence of ruthenium nitro complex and aqueous base, whereby the net effect is to neutralize the base and oxidize a substrate. (J.A.C.S. 99:14/July 6, 1977—Keene et al.)

Also disclosed is production of metal nitrito compounds wherein at least one nitrito group is covalently bonded to at least one metal atom. Such compounds, e.g. those with iron or copper, are shown to catalyze oxidation of molecules such as methane or propylene (U.S. Pat. No. 3,989,801 of Nov. 2, 1976 to B. O. Field et al.)

SUMMARY OF THE INVENTION

In the present process, by proper choice of conditions and additives, any one of a variety of oxidizable structures can be selectively oxidized to a specific oxidation product as the prinicpal product. In particular, secondary alcohols can be thus oxidized to ketones.

We have found that metal nitro complexes are effective oxygen carriers. Accordingly when an oxidizable substrate is provided, in liquid phase, and such metal nitro complex of a transition metal is provided in the oxidation reaction mixture, the nitro ligand of said complex can oxidize the substrate and thus be reduced to a nitrosyl ligand. Under certain conditions the resulting nitrosyl ligand can be reoxidized to nitro ligand by maintaining a molecular oxygen atmosphere over said reaction mixture; i.e. the metal nitro complex functions as a catalyst for the oxidation of the substrate. Otherwise, the nitro ligand, after reduction to nitrosyl ligand in the oxidation process of this invention, can be reoxidized by use of molecular oxygen in presence of an added base, thereby enabling a cyclic process of oxidation with molecular oxygen as the oxygen source to be carried out.

DRAWINGS

This invention is not susceptible of illustration by a drawing.

DETAILED DESCRIPTION

To describe now more particularly the details of our invention, the transition metal which forms the central atom of the metal nitro complex oxidizer is a Group VIII metal such as in particular, cobalt, rhodium, ruthenium, nickel. The metal nitro complexes useful as oxidizers in accordance with our invention can be represented by the general formula $M(L_4)(B)NO_2$, "M" being a transition metal, "$L_4$" being any combination of monodentate, bidentate, tridentate and tetradentate ligands such as to provide four bonding sites, "B" being a monodentate base ligand and "$NO_2$" being the nitro ligand, $-N(=O)O$. Particularly useful is the complex wherein M is $Co^{3+}$, L is saloph ligand of formula $[1,3(ortho-OC_6H_4CH=N)_2C_6H_4]^{2-}$ and B is pyridine. Other complexes which are useful in our process are cobalt complexes derived from oxygen, nitrogen and sulfur donor atoms. The ligand can be tetradentate, for example saloph, salen i.e. $[1,2-(ortho-OC_6H_4CH=N)_2C_2H_4]^{2-}$, (N,N'-ethylenebis(monothioacetylacetoniminate)$^{2-}$, phthalocyanin$^{2-}$ and tetraphenyl porphyrin$^{2-}$. Also the ligand can be bis-bidentate, for example bis(dimethyldithiocarbamate)$^-$, bis(dimethylglyoximate)$^-$, bis(dicyano-1,2-dithiolene)$^-$, bis(ethylene diamine) and bis(acetylacetonate)$^-$. The ligands can also be tetrakis monodentate ligands such as ammonia. Such complexes can be prepared by the same or similar procedures as used in the prior art, such as the above cited Inorganic Chemistry article. The quantity of such complex used is not critical and can be as much as equimolar with the compound to be oxidized, or can be down to a small fraction of that quantity as shown in the Examples below.

Our complexes can be activated and thereby become effective at lowered reaction temperatures, we have found, when a cocatalyst is provided as an additive in the reaction mixture. Cocatalysts which can be used include complexes of $Mo^{6+}$, $W^{6+}$, $V^{5+}$, $Sn^{4+}$, $Al^{3+}$, $B^{3+}$, $Ga^{3+}$; and more generally an organic complex of a transition metal, or a Lewis acid such as a compound of a metallic element with an element of Group VII. The compounds molybdenum dioxide (dialkyl dithiocarbamate) and boron trifluoride are representative of such catalysts which can be used in our process. The quantity of cocatalyst used is not critical and can be much less or much more, on a molar basis, than the quantity of nitro complex used.

Substrates which we have found amenable to oxidation by our process include easily oxidizable materials such as triphenylphosphine; and more difficultly oxidizable materials such as secondary alcohols and compounds having isolated olefinic bonds. When such more difficultly oxidizable compound is the substrate, it is advantageous to activate the metal nitro complex by use of a Lewis acid such as boron trifluoride etherate. When specifically a compound having an isolated olefinic bond is the substrate to be oxidized, a useful activator is divalent palladium in form of a complex with said olefinic bond.

When our process is used to oxidize a secondary alcohol, the principal oxidation product is the ketone having the same skeletal structure as said secondary alcohol. In particular, cyclic alcohols such as the cyclopentanols, cyclohexanols, cycloheptanols and cyclooctanols, substituted and unsubstituted can be oxidized to the corresponding ketones, namely cyclopentanone, cyclohexanone, cycloheptanone and cyclooctanone, respectively.

Conjugated dienes can be oxidized by metal nitro complexes in accordance with our process whereby to obtain, from a conjugated diene such as 1,3-cyclohexadiene, the aromatic product, benzene.

The following examples are illustrative of our invention and of the best mode we now contemplate for carrying out the invention, but are not to be interpreted as limiting.

EXAMPLE 1

81.7 mg. (0.164 mmol) of cobalt (saloph) pyridine nitro complex and 187 mg. (0.713 mmol) of triphenylphosphine were dissolved in 20 ml. of 1,2-dichloroethane together with 0.5 ml. of pyridine. (The saloph ligand is the tetradentate ligand $[1,2\text{-}(ortho\text{-}OC_6H_4CH=N)_2C_6H_4]^{2-}$ obtained by condensation reaction of o-diaminobenzene with salicylaldehyde). The resulting solution was stirred under an oxygen atmosphere for 18 hours at 60° C. The resulting reaction product was analyzed by infrared spectroscopy showing a quantitative yield of triphenylphosphine oxide, i.e. 0.713 mmol. This example is illustrative of catalytic oxidation by a cobalt nitro complex having a tetradentate ligand and a monodentate basic ligand in accordance with this invention.

EXAMPLE 2

The molybdenum complex, molybdenum monoxide (dipropyl dithiocarbamate) of formula $MoO[(S_2CNCH_2CH_2CH_3)_2]_2$ was oxidized using the same cobalt nitro complex employed in Example 1, with formation of the dioxide $MoO_2[S_2CN(CH_2CH_2CH_3)_2]_2$. The simultaneous production as coproduct of the cobalt (saloph) nitrosyl complex was shown by the presence of the nitrosyl band in the infrared spectrum of the product. Specifically, the molybdenum complex (192 mg.) and the cobalt nitro complex (91 mg.) were dissolved in deaerated 1,2-dichloroethane; and the solution was stirred under argon at 60° C. for a total of 1.5 hours, and was then evaporated to dryness by pumping off the vapors, and analyzed.

EXAMPLE 3

50 mg. of the cobalt nitro complex of Example 1 (0.101 mmol) and 58 mg. (0.157 mmol) of molybdenum dioxide (dimethyl dithiodicarbamate) were dissolved together with 12 mg. (0.105 mmol) of cycloheptanol in 10 ml. of 1,2-dichloroethane, with deaeration by a stream of argon. The solution was stirred under argon atmosphere at 75° C. After 70 minutes, formation of cycloheptanone in about 50% yield and cobalt (saloph) nitrosyl complex were detected.

Cyclohexanol can be oxidized to cyclohexanone by essentially this same procedure.

EXAMPLE 4

41.8 mg. of the cobalt (saloph) pyridine nitro complex of Example 1 ($8.39\times10^{-5}$ mol), 127 mg. of cycloheptanol ($111\times10^{-5}$ mol) and 34.7 mg. of BF$_3$ etherate ($24.5\times10^{-5}$ mol) were dissolved under a dry argon atmosphere in 10 ml. of dry 1,2-dichloroethane. The solution was vigorously deaerated with argon gas. The reaction vessel was stoppered and immersed in a 70° C. oil bath. After 10 minutes, cycloheptanone was identified in the products in quantitative yield based on the cobalt nitro complex initially employed. The cycloheptanone was identified by cooling the solution in ice and subjecting it to gas chromatographic analysis.

The reaction product was evaporated to dryness by pumping. The solid residue showed, by infrared, a band identified as that of the nitrosyl ligand with cobalt, but shifted to slightly higher wave lengths (namely about 1690 wave numbers versus 1665 for the cobalt (saloph) nitrosyl complex). The shift is believed due to formation of an addition compound of the complex with boron trifluoride.

The solid material was dissolved in about 30 ml. of dichloromethane and filtered. To the filtrate, about 0.3 ml. of pyridine was added and the solution was stirred at room temperature while bubbling oxygen in. Within a few minutes a change to the orange-red color of the cobalt nitro complex was observed. The operation was continued for 2 hours, then the resulting solution was pumped to dryness. The solid residue, examined by infrared, no longer showed a band at 1690 wave numbers but showed the characteristic bands at 1220, 1320 and 820 for the complex, cobalt (saloph) pyridine nitro complex. This example illustrates how the cobalt nitro complex can function as an oxygen carrier, with added Lewis acid (namely boron trifluoride etherate) as activator, and then the resulting coproduct, the cobalt nitrosyl complex, can be reoxidized in presence of base (pyridine) by molecular oxygen to the starting cobalt nitro complex.

Cyclohexanol can be oxidized to cyclohexanone by essentially this same procedure.

EXAMPLE 5

46.4 mg. of the same cobalt nitro complex as in the preceding Examples was dissolved in 10 ml. of deaerated 1,2-dichloroethane. There was added 0.3 ml. of cyclohexadiene and 0.03 ml. of BF$_3$ etherate. A solid precipitated immediately. As before, the liquid reaction mixture was deaerated with argon and the vessel was stoppered. The product obtained after 10 minutes heating under argon in a 60° C. oil bath was analyzed by gas chromatography, showing a peak which matches the peak for coinjected authentic benzene. After 1 hour, this peak had increased by about 3 fold.

The product was evaporated to dryness by pumping off the gases. Infrared analysis indicated presence of boron trifluoride/cobalt nitrosyl complex. Upon thin layer chromatographic analysis in 5% methanol/chloroform, the "RF" value was found to be about 0.8 and identical to that of authentic cobalt nitrosyl complex.

We claim:

1. In a process of oxidizing an oxidizable substrate in liquid phase using molecular oxygen as the oxygen source, the improvement which comprises providing in the oxidation reaction mixture a transition metal nitro complex, representable by the general formula M(L$_4$)BNO$_2$ wherein M is a transition metal, L$_4$ is any combination of monodentate, bidentate, tridentate, and tetradentate ligands, such as to provide four bonding sites, B being a monodentate base ligand and NO$_2$ being the nitro ligand —N(=O)O, under conditions such that the nitro ligand of said complex can oxidize the substrate and thus be reduced to a nitrosyl ligand; and establishing conditions such that such nitrosyl ligand can be reoxidized by molecular oxygen to nitro ligand.

2. Process of claim 1 wherein the transition metal of the nitro complex is a Group VIII metal.

3. Process of claim 2 wherein the Group VIII metal is cobalt.

4. Process of claim 2 wherein, "$L_4$" is a tetradentate ligand, "B" being a monodentate base ligand.

5. Process of claim 4 wherein M is $Co^{3+}$, $L_4$ is saloph ligand of formula $[1,3\text{-}(ortho\text{-}OC_6H_4CN=N)_2C_6H_4]^{2-}$ and B is pyridine.

6. Process of claim 5 wherein a molecular oxygen atmosphere is maintained over said oxidation reaction mixture whereby a concentration of metal nitro complex, effective to bring about oxidation of the substrate, is maintained in the reaction mixture.

7. Process of claim 5 wherein a cocatalyst is provided as an additive in the reaction mixture, said cocatalyst being an organic complex of $Mo^{6+}$, $W^{6+}$, $V^{5+}$, $Sn^{4+}$, $Al^{3+}$, $B^{3+}$, or $Ga^{3+}$ or a Lewis acid compound of a metallic element and an element of Group VII.

8. Process of claim 7 wherein the substrate oxidized is a secondary alcohol, the cocatalyst is $BF_3$ etherate and the principal oxidation product is the ketone having the same skeletal structure as said secondary alcohol.

9. Process of claim 8 wherein the secondary alcohol is cyclohexanol and the principal oxidation product is cyclohexanone.

10. Process of claim 8 wherein the secondary alcohol is cycloheptanol and the principal oxidation product is cycloheptanone.

11. Process of claim 5 wherein the substrate oxidized is a conjugated diene.

* * * * *